United States Patent [19]

Steele et al.

[11] Patent Number: 5,693,472

[45] Date of Patent: Dec. 2, 1997

[54] **DETECTION OF *CRYPTOSPORIDIUM PARVUM***

[75] Inventors: Marilyn I. Steele, Edmond; Thomas L. Kuhls, Oklahoma City; S. Kay Nida, Edmond, all of Okla.

[73] Assignee: The Board of Regents of the University of Oklahoma

[21] Appl. No.: 473,157

[22] Filed: Jun. 7, 1995

[51] Int. Cl.$^6$ .............................. C12Q 1/68; C12P 19/34; C07H 21/02; C07H 21/04
[52] U.S. Cl. ........................ 435/6; 435/91.2; 536/23.1; 536/24.3; 536/24.33
[58] Field of Search .................. 435/6, 91.2; 536/23.1, 536/24.3–24.33

[56] References Cited

FOREIGN PATENT DOCUMENTS

| | | |
|---|---|---|
| 4408700 | 4/1995 | Germany . |
| 9323563 | 11/1993 | WIPO . |
| 9324649 | 12/1993 | WIPO . |
| 9402635 | 2/1994 | WIPO . |
| 9404681 | 3/1994 | WIPO . |

OTHER PUBLICATIONS

Knapp et al., "Protection Of Aotus Monkeys From Malaria Infection By Immunization With Recombinant Hybrid Proteins", *Infection and Immunity*, Jun. 1992, pp. 2397–2401.
Webster et al., "Detection of *Cryptosporidium parvum* Using A Specific Polymerase Chain Reaction", *Veterinary Parasitology*, 50 (1993) 35–44.

M. Steele; T. Kuhls; D. Mosier; K. Nida; W. Elliott; "Identification of a *Cryptosporidium parvum* Genomic Region that Encodes a Protein Which Manifests Hemolytic Activity"; University of Oklahoma Health Sciences Center; Oklahoma City, OK, USA; 94th General Meeting of the American Society for Microbiology, Las Vegas, Nevada, USA, May 23–27, 1994. Abstracts of the General Meeting of the American Society for Microbiology 94; 1994.

J. Protozool., vol. 38, No. 6, Nov. 1991, pp. 74s–76s, XP000615257, Kuhls et al.: "Effects of Carbohydrates and Lectins on Cryptosporidial Sporozoite Penetration of Cultured Cell Monolayers".

American Journal of Tropical Medicine & Hygiene, vol. 45, No. 6, 1991, pp. 688–694, XP000405969, Laxer et al.: "DNA Sequences for the Specific Detection of *Cryptosporidium Parvum* by the Polymerase Chain Reaction".

Dykstra et al. J. of Protozool. 38: 76S–78S, 1991.

*Primary Examiner*—W. Gary Jones
*Assistant Examiner*—Dianne Rees
*Attorney, Agent, or Firm*—Dunlap & Codding, P.C.

[57] ABSTRACT

A method and kit for the detection of *Cryptosporidium parvum* in aquatic and biological samples such as surface water or feces. The method relies on the use of primers to detect all or a portion of at least one DNA sequence characteristic of *C. parvum*, the sequence being all or part of the genomic regions referred to as 38G and HemA contained within recombinant plasmids pINV38G, and pHem4, respectively.

33 Claims, No Drawings

DETECTION OF CRYPTOSPORIDIUM PARVUM

The present invention relates to a method for the detection and/or identification of organisms and/or nucleic acid sequences of Cryptosporidium parvum (C. parvum) and to oligonucleotides and test kits containing them for use in said method.

Cryptosporidium parvum (phylum Apicomplexa) is a coccidian protozoan capable of parasitizing the intestinal tract of a variety of mammalian species. First recognized as a veterinary pathogen, its importance as a cause of human disease was not appreciated until the development of the acquired immunodeficiency syndrome epidemic. C. parvum is now recognized as a significant cause of diarrheal disease in both immunosuppressed and immunocompetent people worldwide. The disease has an incubation period of 1–14 days with symptoms lasting for 7–60 days. This intestinal pathogen has also been shown to play a significant role in the vicious diarrhea/malnutrition cycle experienced by young children in developing countries. Numerous outbreaks of cryptosporidiosis have been reported in the United States associated with person-to-person contact in day-care centers and hospitals, and waterborne spread from contaminated public water supplies. Resistance to chlorination and lack of an effective treatment contribute to the organism's spread.

C. parvum exists in nature in the form of environmentally resistant, thick walled oocysts. Large numbers of oocysts have been recovered from waste surface and recreational waters, but their origin is unknown. These oocysts have been known to survive for considerable periods in water and are unaffected by conventional water treatments. After ingestion, motile sporozoites released from the oocysts by the action of bile acids within the gut lumen invade the epithelial cells lining the intestine, form parasitophorous vacuoles beneath the microvillus membranes of these host cells, and initiate a complex life cycle containing both sexual and asexual reproductive stages. C. parvum sporozoites contain an apical complex consisting of rhopteries, micronemes, and preconoidal rings which are believed to play a key role in host cell invasion. It has been postulated that proteins secreted from the apical complex of these life stages initiate alterations in enterocyte membranes that lead to successful intracellular localization of the parasite. Very little is known about the molecular mechanisms for adherence to and penetration of intestinal epithelial membranes by cryptosporidial sporozoite life stages. Identification of specific sporozoite invasion factors could provide sensitive targets for more effective treatment strategies. Unfortunately, the lack of efficient laboratory culture methods to obtain large quantities of C. parvum has hampered efforts to directly isolate and characterize cryptosporidial proteins expressed during host cell parasitization. Proteins involved in the invasive processes of other intracellular pathogens have been indirectly identified by cloning genomic regions from these organisms into nonpathogenic Escherichia coli strains and screening the transformants for the ability to invade cultured cell lines and escape subsequent antibiotic exposure. The utilization of gentamicin survival assays to identify invasive proteins from human pathogens was first described in studies of Yersinia pseudotuberculosis invasion. Since that time, proteins involved in the invasive mechanisms of Yersinia enterocolitica and Mycobacterium tuberculosis have been identified in a similar manner.

DESCRIPTION OF THE INVENTION

ISOLATION OF THE 38G GENOMIC REGION

A C. parvum genomic expression library was transformed in E. coli XL1-Blue and the transformants were tested for invasive activity in gentamicin survival assays using an intestinal-like epithelial cell line. Described herein is the identification and characterization of a 1.3 kb C. parvum genomic region which induces invasive activity in a non-pathogenic E. coli strain.

Materials and Methods

Library formation. C. parvum oocysts were obtained from infected Holstein calves and purified as described by Kuhls, et al. (J. Protozool, 1991, 38:74S–76S). Approximately $2 \times 10^9$ oocysts were freeze-thawed eight times in liquid nitrogen and incubated overnight at 55° C. in lysis buffer (120 mM NaCl, 10 Mm EDTA, 25 mM Tris Ph 7.5, 1% Sarkosyl) containing 1 mg/ml proteinase K. Nucleic acids isolated by phenol/chloroform extraction and ethanol precipitation were treated with Rnase to remove co-precipitating RNA. EcoRI linkers were ligated to randomly sheared chromosomal DNA and a library consisting of $6.3 \times 10^6$ primary recombinants was constructed in the EcoRI site of the Lambda ZAP II expression vector (Stratagene). A representative portion of the phage library was excised with R408 helper phage to generate subclones in the pBluescript SK-phagemid vector which were transformed in competent E. coli XL1-Blue cells.

Gentamicin Survival Assay. Intestine 407 (ATCC CLL-6) monolayers were maintained in RPMI-1640 medium with 5% fetal calf serum. The monolayers were incubated for 3 hours at 37° C. with E. coli XL1-Blue library transformants at a ratio of 100 bacteria per cell. After incubation, the monolayers were washed several times with sterile phosphate buffered saline (Ph 7.4) and incubated in fresh media containing 75 ug/ml gentamicin for 1.5 hours at 37° C. to destroy any remaining extracellular bacteria. The cells were lysed with 0.5% Triton X-100, and the cell lysates were plated on L agar containing 100 ug/ml ampicillin for identification and quantitation of surviving transformant strains. In the initial screening of the C. parvum genomic library, $1.6 \times 10^5$ E. coli XL1-Blue transformants were tested. Those strains surviving the first assay were scraped from the agar plates, reincubated with fresh tissue culture cells, and assayed again. Survivors from this second round were tested a third time. In assays testing individual transformants, plate counts of the original inoculums were performed in order to determine a survival rate for each transformant. Survival rates were calculated as follows: 100×[number of bacteria present in cell lysates/number of bacteria added to monolayers].

Sequence analysis. Nucleotide sequences were determined utilizing $^{32}$P end-labeled primers with the fmol DNA Sequencing System (Promega) according to the manufacturer's instructions. T3 and T7 sequencing primers were provided in the kit and additional primers were synthesized by the Molecular Biology Resource Facility of St. Francis Hospital located at the University of Oklahoma Health Sciences Center. Homology searches and sequence analysis were performed using the University of Oklahoma Genetics Computer Group sequence analysis software package (version 6.0) from the University of Wisconsin Biotechnology Center.

Analysis of plasmid encoded polypeptides. [$^{35}$S] methionine labeled plasmid encoded translational products were expressed in maxicells of E. coli CSR603 using the method described by Sancar, et al., (J. Mol. Biol., 1981, 148:45–62). Cell lysates were separated by SDS-PAGE (Laemmli, U., Nature, 227:680–685) on a 16.5% gel, and proteins were visualized by exposure to Kodak X-Omat AR film.

Pulsed Field Gel Electrophoresis. Oocysts were prepared for electrophoresis by the method described by Mead et al., (J. Parasitol, 1988, 74:366–369. Briefly, $1\times10^8$ purified oocysts were washed and resuspended in 50 µl of suspension buffer (75 Mm $NaPO_4$, 65 Mm NaCl 1% glucose), Ph 8.0. Then 50 µl of 1% low gelling temperature agarose (SeaPlaque GTG, FMC BioProducts, Rockland, Me.) previously melted in suspension buffer and cooled to 37° C. was added and 100 µl aliquots of the mixture were placed into molds on ice to gel. After solidification, each agarose block was incubated in 10 ml of lysis buffer (0.5 M EDTA, 1.0% sodium N-lauroylsarcosine, 2.0 mg/ml proteinase K), Ph 9.5, at 50° C. for 48 hours. The blocks were then washed extensively and stored in 50 Mm EDTA, 10 Mm Tris Ph 8.0 at 4° C. Agarose blocks were cut in half and loaded into the slots of a 0.7% agarose (Pulse Field Certified Agarose, BioRad) gel in 45 Mm Tris, 45 Mm boric acid, 1.25 Mm ethylenediamine tetraacetic acid buffer, Ph 8.0 (TBE). The DNA was fractionated on a CHEF-DR III pulsed field electrophoresis system (BioRad). Gels were run at 14° C. for 40 hours with a voltage of 6v/cm, an angle of 120°, and switch time from 60–120 seconds. After depurination in 0.25M Hcl, the gels were washed, and blotted by capillary transfer to Zeta-Probe GT nylon membranes (Bio-Rad). The membranes were hybridized with a $^{32}$P-labeled 1.3 kb fragment according to instructions supplied by the manufacturer and exposed to Kodak X-Omat AR film.

Electron microscopy. INT 407 monolayers were incubated for varying times periods with the transformants as described above. After several washings with phosphate buffered saline, the monolayers were fixed in 2% paraformaldehyde-2.5% glutaraldehyde in cacodylate buffer, and routinely processed for transmission and scanning electron microscopy.

RNA isolation and RT-PCR. C. parvum sporozoites were excysted from purified oocysts and prepared as previously described (Kuhls et al., J. Protozool, 38:74S–76S). The sporozoites were frozen overnight at −70° C. in guanidinium isothiocyanate denaturing solution supplied in the RNA Isolation Kit (Stratagene, La Jolla, Calif.) and ground exhaustively in a cold mortar and pestle kept at −70° C. Total RNA was extracted according to the kit instructions. Isolated RNA was incubated at a concentration of 1 unit/µg of Rnase free Dnase (Stratagene) for one hour at 37° C. to remove any contaminating DNA.

RT-PCR was performed on 650 ng of total sporozoite RNA per reaction with the reagents and instructions provided in the SUPERSCRIPT Preamplification System (Gibco/BRL, Gaithersburg, Md.). Random hexamers were used to prime first strand cDNA synthesis. PCR amplifications were performed in a 100 µl reaction mixture containing 50 pmoles of each primer and 5 units of Taq DNA polymerase (Gibco/BRL) per reaction with the following cycling parameters: initial denaturation at 94° C. for 5 min, followed by 40 cycles of 94° C. for 1 min, 50° C. for 30 sec, 72° C. for 3 min, and a final 8 min extension at 72° C. The reactions were performed in a Perkin-Elmer model 480 thermocycler (Perkin-Elmer Cetus, Norwalk, Conn.). Negative control reactions omitting the reverse transcriptase were run with each sample to ensure that the PCR products were not due to amplification of contaminating sporozoite DNA. Positive control reactions using primers specific to the C. parvum actin gene were performed to verify the integrity of the isolated RNA and the suitability of the reaction conditions. Actin primers were designed based on the reported sequence of a C. parvum actin gene, GenBank accession number M69014. The forward primer covers positions 365–384 and the reverse primer covers positions 659–640 of the deposited nucleotide sequence. All oligonucleotides in this study were synthesized at the Molecular Biology Resource Facility, St. Francis Medical Research Institute, University of Oklahoma Health Science Center.

Results

Screening the bacterial transformants. Invasive activity was measured by testing the ability of the bacterial transformants to survive gentamicin exposure after incubation with Intestine 407 monolayers. Transformant strains closely associating with or penetrating the intestinal cell membranes were expected to be protected from the antibiotic. Seventy-six recombinant XL1-Blue transformants survived the three serial gentamicin survival assays. Recombinant plasmids isolated from sixty (79%) of these strains contained a 4.1 kb insert with identical restriction patterns demonstrated by agarose gel electrophoresis. Transformants containing this recombinant plasmid, designated pINV38G, were then tested individually in the survival assay along with strains containing nonrecombinant pBluescript and a recombinant pBluescript, pNHEM9, which was randomly selected from the plasmid library. pINV38G transformants consistently demonstrated a capacity for gentamicin survival 500–to 4000-fold higher than pBluescript and pNHEM9 transformants (see Table 1).

TABLE I

Relative Survival of Transformants After Gentamicin Exposure of Intestine 407 Monolayers

| INFECTING STRAIN | RELATIVE SURVIVAL* |
|---|---|
| XL1-Blue (pBluescript) | 1 |
| XL1-Blue (PINV38G) | 500–4000 |
| XL1-Blue (pINV38G1.3) | 30–400 |
| XL1-Blue (pNHEM9) | 0.8–3 |

*Relative survival values were determined by dividing the survival rate of the infecting strain by the survival rate of XL1-Blue (pBluescript). Survival rates = 100 × (# bacteria present after gentamicin exposure/# bacteria added to Intestine 407 monolayers). The ranges indicated reflect the results from several experiments.

Characterization of the cryptosporidial segment. Restriction mapping and nucleotide sequence analysis of the recombinant clone demonstrated that the 4.1 kb insert contained a 1.5 kb segment of pBluescript which was flanked on each side by identical 1.3 kb C. parvum genomic fragments. To establish that the survival phenotype of the pINV38G transformants was encoded on the 1.3 kb segment, gentamicin survival assays were performed with XL1-Blue cells freshly transformed with recombinant clones, designated pINV38G1.3, containing a single copy of the 1.3 kb region. These transformants demonstrated a lower level of gentamicin survival than XL1-Blue(pINV38G), but survival was consistently 30–to 400-fold higher than that of pBluescript and pNHEM9 transformants (Table 1).

The nucleotide sequence of the 1.3 kb (38G) fragment had A+T content of 73%, consistent with that reported for other cryptosporidial genomic sequences. Computer analysis predicted several small open reading frames none of which appeared to have had significant homology to other reported sequences. Karyotypic Southern blot analysis of C. parvum chromosomal DNA fractionated by pulsed field gel electrophoresis mapped the 1.3 kb segment to the smallest of five fractionated C. parvum chromosomes. To identify protein products encoded by the 1.3 kb region, the recombinant plasmids were tested in maxicells. A radiolabeled protein of ca. 5,800 daltons was detected on autoradiographs of maxicell lysates from pINV38G and pINV38G1.3 transformants, but not in lysates from transformants containing pBluescript. The size of this protein is consistent with the size of two open reading frames predicted from the nucleotide sequence of the 1.3 kb fragment.

Electron microscopy of infected monolayers. To determine whether the bacterial transformants were actually internalized, both scanning and transmission electron microscopy were performed on Intestine 407 monolayers incubated from one to three hours with XL1-Blue (pINV38G) and XL1-Blue(pBluescript). The monolayers were washed extensively after the incubation periods, but gentamicin was omitted in order to ensure that adequate numbers of bacteria would be present for observation and comparison. After one and two hour incubations, most of pINV38G transformants were only loosely associated with Intestine 407 cellular processes, however, some were more closely associated with the plasma membrane, and had one end turned toward the monolayers. After three hours, substantial numbers of bacteria had one end partially embedded into the intestinal cell membranes. The portion of each bacterium which was embedded ranged from <10% to 50% Although portions of some bacteria were completely encircled by cell membrane and cytoplasm, the bacteria remained extracellular and were separated from the cytoplasm by plasma membrane in all areas observed. In contrast, although a similar number of bacteria were observed in all incubation periods with XL1-Blue (pBluescript), this nonrecombinant transformant remained only loosely associated with the Intestine 407 cells throughout three hours of incubation. In general, intestinal cell morphology was similar between the two samples studied, but monolayers exposed to pINV38G transformants had more cells which appeared damaged. These cells contained smoother surfaces (loss of cellular processes) and were more rounded than uninfected cells. pINV38G transformants were not seen embedded into the damaged cells.

Gentamicin survival in other tissue culture cell lines. To determine whether the invasive activity demonstrated by XL1-Blue (pINV38G) was specific to Intestine 407 monolayers, survival assays using other epithelial cell lines were performed. Compared to gentamicin survival present after incubation with Intestine 407 monolayers, XL1-Blue transformants demonstrated a five- to ten-fold higher level of survival in WISH cells, an equivalent level in Hep-2 cells, a hundred-fold lower level in IEC-6 cells and no detectable survival in MDCK cells.

RT-PCR analysis of sporozoite RNA. Cryptosporidial genomic regions encoding proteins necessary for host cell entry should be actively transcribed in C. parvum sporozoites. To determine whether transcripts homologous to the 1.3 kb region were present in this life stage, total RNA isolated from C. parvum sporozoites was analyzed in RT-PCR reactions using a primer pair that was specific to an open reading frame in the 1.3 kb region. These primers are a forward primer shown in SEQ ID NO:5 and a reverse primer shown in SEQ ID NO:6. The anticipated amplification product of 152 bp expected from the primer pair was demonstrated on agarose gel electrophoresis of the RT-PCR reaction. The bands were excised from the gel and analyzed by nucleotide sequence analysis for verification of the PCR products.

Open Reading Frames

Bases 423 through 560 and bases 1134 through 1298 in SEQ ID NO:1. constitute a first and second open reading frame, respectively, in SEQ ID NO:1. Each of these open reading frames codes for a protein which can be used to detect the presence of C. parvum.

ISOLATION OF HEMA GENOMIC REGION

A C. parvum genomic expression library was transformed into a nonpathogenic Escherichia coli strain, and the transformants were screened on blood agar to identify hemolytic strains. Described herein is the cloning and characterization of a cryptosporidial genomic region (HemA) which confers a hemolytic phenotype on *E. coli* XL1-Blue.

Materials and Methods

Library formation. Cryptosporidial oocysts were obtained from experimentally infected Holstein calves and purified as previously described. Approximately $2\times10^9$ oocysts were freeze-thawed eight times with liquid nitrogen and incubated overnight at 55° C. in lysis buffer (120 mM NaCl, 10 Mm EDTA, 25 mM Tris Ph 7.5, 1% Sarkosyl) containing 1 mg/ml proteinase K. Nucleic acids isolated by phenol/chloroform extraction and ethanol precipitation were treated with Rnase to remove co-precipitating RNA. EcoRI linkers were ligated to randomly sheared chromosomal DNA and a library consisting of $6.3\times10^6$ primary recombinants was constructed in the EcoRI site of the Lambda ZAP II expression vector (Stratagene). The phage library was excised with R408 helper phage to generate subclones in the pBluescript$^{SK-}$ phagemid vector.

Subcloning and sequence analysis. Unidirectional deletion clones were generated using exonuclease III (Stratagene) according to the manufacturer's instructions. Exonuclease III resistant sites were created by NotI digestion of the recombinant plasmid followed by end-filling with thioderivatives, and sensitive sites were created by digestion with BamHI. Nucleotide sequences were determined utilizing $^{32}P$ end-labeled primers with the fmol DNA Sequencing System (Promega). The T3 and T7 sequencing primers were provided with the kit and all additional primers were synthesized by the Molecular Biology Resource Facility of St. Francis Hospital located at the University of Oklahoma Health Sciences Center.

Analysis of plasmid encoded polypeptides. Proteins encoded on H4 and the H4 deletion clones were identified by expression in maxicells of *E. coli* CSR603 by the procedure described by Sancar (*J. Bact.*, 1979, 137:692–693). Maxicell lysates were separated by SDS-PAGE on a 12.5% gel, and proteins were visualized by autoradiography on Kodak X-Omat AR film.

Pulsed Field Gel Electrophoresis. Cryptosporidial oocysts were prepared for electrophoresis by the method described by Mead (*J. Parasitol*, 1988, 74:366–369). Briefly, $1\times10^8$ purified oocysts were washed and resuspended in 50 μl of suspension buffer (75 Mm $NaPO_4$, 65 mM NaCl, 1% glucose), pH 8.0. Fifty microliters of 1% low gelling temperature agarose (SeaPlaque GTG, FMC BioProducts, Rockland, Me.) previously melted in suspension buffer and cooled to 37° C. was added and 100 μl aliquots of the mixture were placed into molds on ice to gel. After solidification, each agarose block was incubated in 10 ml of lysis buffer (0.5 M EDTA, 1.0% sodium N-lauroylsarcosine, 2.0 mg/ml proteinase K), pH 9.5, at 50° C. for 48 hours. The blocks were then washed extensively and stored in 50 mM EDTA, 10 mM Tris pH 8.0 at 4° C. Agarose blocks were cut in half and loaded into the slots of a 0.7% agarose (Pulse Field Certified Agarose, BioRad) gel in 22 mM Tris, 22 mM boric acid, 0.62 mM EDTA buffer, pH 8.0. The DNA was fractionated on a CHEF-DR III pulsed field electrophoresis system (BioRad). Gels were run at 14° C. for 40 hours with a voltage of 6 v/cm, an angle of 120°, and switch time from 60–120 seconds. After depurination in 0.25M HCl, the gels were washed, and blotted by capillary transfer to Zeta-Probe GT nylon membranes (BioRad). The membranes were hybridized with a $^{32}$P-labeled 5.5 kb fragment according to instructions supplied by the manufacturer and exposed to Kodak X-Omat AR film.

Hemolytic assays. Overnight cultures of H4 and pBluescript XL1-Blue transformants were grown in 5 ml of terrific broth containing 100 µg/ml ampicillin. After centrifugation, the culture supernatants were kept on ice until tested. The cell pellets were washed in sterile phosphate buffered saline (PBS), resuspended in 1 ml PBS, sonicated on ice and centrifuged to remove insoluble membranes. Sheep erythrocytes were washed in PBS and brought up to a 5% v/v suspension in PBS. For each assay, 500 µl of the test sample was incubated with an equal volume of 5% sheep erythrocyte suspension for 4 hr at 37° C. After centrifugation, the release of free hemoglobin was measured by reading the optical density of the supernatant at 540 nm. The values for 0% and 100% erythrocyte lysis were determined by the addition of PBS and 0.1% Triton-X 100, respectively, to an equal volume of 5% sheep erythrocytes. Sonicates were tested directly, after diluting 1:10 with PBS, in PBS containing 10 mM MgCl$_2$ or 10 mM EDTA, and in 10 mM Tris-HCl (pH7.2), 150 mM NaCl (TBS) containing 10 mM CaCl$_2$. For assays in the presence of added Ca$^{++}$, the sheep erythrocytes were resuspended in TBS and sonicate dilutions were made with TBS. Sonicates were assayed after heat treatment at 60° C. for 30 min and after incubation with 200 µg proteinase K for 1 hr at 37° C. Protein concentrations in the sonicate supernatants were determined by the method used by Smith et al. (*Anal. Biochem.*, 150:76–85, 1985).

RNA isolation. RNA was isolated from purified *C. parvum* sporozoites that were prepared as previously described (Kuhls et al., *J. Protozool*, 1991, 38:74S–76S). The sporozoites were frozen overnight at –70° C. in guanidinium isothiocyanate solution and then ground exhaustively with a cold mortar and pestle. Total RNA was isolated by phenol/chloroform extraction and incubated with RNase-free DNase (Stratagene) at a concentration of 1 unit/µg for one hour at 37° C. to remove contaminating DNA.

Male and female 6-week-old C.B-17Icr scid/scid (SCID) mice were given intragastric inoculations of 2×10$^6$ purified cryptosporidial oocysts as previously described (Kuhls et al., *J. Comp. Pathol.*, 1992, 106:399–410). Three uninfected and three infected mice were killed by CO$_2$ inhalation at 60 days post inoculation and the ascending colons were removed, opened longitudinally and flushed to remove fecal debris. The ascending colons of one uninfected and infected SCID mouse was fixed in 10% buffered formalin for histopathologic analysis. The remaining colonic segments were stored immediately at –70° C. The frozen intestinal tissues were ground exhaustively in guanidinium isothiocyanate solution and total cellular RNA was isolated by phenol/chloroform extraction with incubation in RNase-free DNase as described above.

RT-PCR. For cDNA synthesis, 1 µg of sporozoite RNA or 3 µg of murine intestinal RNA was incubated for 1 hour at 42° C. in a 20 µl reaction mixture containing 50 mM Tris-HCl (pH 8.3), 75 mM KCl, 3 mM Mg Cl$_2$, 0.4 µg random hexamers (Gibco/BRL), 10 mM of each deoxynucleotide triphosphate, 20 units placental ribonuclease inhibitor (Gibco-BRL) and 200 units Moloney murine leukemia virus reverse transcriptase (Gibco-BRL). The samples were then heated at 94° C. for 5 minutes, diluted to a final volume of 100 µl with 0.1% (wt/vol) diethylpyrocarbonate treated water and stored at –20° C. PCR reactions were performed in a 50 µl volume containing 15 µl of the cDNA reaction, 10 mM Tris-HCl (pH 8.3), 50 mM KCl, 1.5 mM MgCl$_2$, 0.01% (wt/vol) gelatin, 50 pmoles of each primer, 10 mM of each deoxynucleotide triphosphate, and 5 unit of Taq DNA polymerase. Twenty-five cycles consisting of 94° C. for 1 min, 65° C. for 2 min, 72° C. for 1 min, and a final 8 min extension at 72° C. were performed. Reaction products were visualized by electrophoresis of 35 µl of the reactions in a 1.5% agarose gel containing 1 µg/ml ethidium bromide. The reactions were performed in a Perkin-Elmer model 480 thermocycler (Perkin-Elmer Cetus, Norwalk, Conn.). Negative control reactions which either omitted the reverse transcriptase or template were performed to ensure that the PCR products were not due to amplification of contaminating DNA. A forward primer for hemA is shown in SEQ ID NO:7. A reverse primer for HemA is shown in SEQ ID NO:8. The cryptosporidial actin primers were designed based on the reported sequence of a *C. parvum* actin gene (Kim et al., *Mol. Biochem. Parasitol*, 1992, 50:105–114), GenBank accession number M69014. The forward primer (SEQ ID NO:7) covers positions 365–384 and the reverse primer (SEQ ID NO:8) covers positions 659–640 of the deposited nucleotide sequence SEQ ID NO:3. The oligonucleotide primers were synthesized at the Molecular Biology Resource Facility, St. Francis Medical Research Institute, University of Oklahoma Health Science Center. The mouse β-actin primers were the same as those used by Buchanan et al. (*Infect. Immun.*, 62:2930–2939, 1994). They flank an intron in the mouse β-actin gene and amplify a 620-bp fragment from murine cDNA.

GenBank accession number. The nucleotide sequence for hemA was deposited in GenBank under accession number U18120.

Results

Identification of pHEM4. A cryptosporidial genomic expression library in the pBluescript phagemid was transformed into *E. coli* XL1-Blue and the transformants were plated on 5% sheep blood agar containing 100 µg/ml ampicillin. After incubation at 37° C. for 24 hours, recombinant strains with a hemolytic phenotype were distinguished by the development of a clear zone around the bacterial colonies. Those strains exhibiting hemolytic activity were restreaked for verification, and four stable hemolytic recombinant strains were identified. Dot blot hybridization studies and restriction mapping determined that two of these strains contained a recombinant clone (designated H4) with the identical 5.5 kb cryptosporidial genomic insert. The H4 transformant exhibited the most striking hemolytic zone on blood agar plates compared to the other two hemolytic strains and was chosen for further analysis. To confirm that the hemolytic activity was encoded on the recombinant plasmid, fresh XL1-Blue cells transformed with H4, pBluescript and a nonhemolytic recombinant clone chosen randomly from the cryptosporidial genomic library were tested on blood agar. The new H4 transformants consistently caused hemolysis while transformants containing pBluescript and the nonhemolytic recombinant plasmid remained nonhemolytic.

Analysis of the H4 cryptosporidial insert. A set of overlapping deletion clones were generated from the 5' end of the 5.5 kb insert using exonuclease III. The subclones were transformed into XL1-Blue and the sizes of the remaining cryptosporidial inserts were determined. Transformants containing various lengths of the insert were plated on sheep blood agar to determine their hemolytic phenotype. Hemolytic activity was still detectable on blood agar after removal of 4.5 kb of the original insert. Nucleotide sequence analysis of the deletion clones demonstrated the presence of a complete 690 bp open reading frame (hemA) located within a 1 kb region at the 3' end of the original insert. XL1-Blue transformants containing subclones of the 5.5 kb insert which included only a portion of hemA did not demonstrate a hemolytic phenotype on sheep blood agar.

The nucleotide sequence of hemA is represented as SEQ ID NO:3 and its complementary sequence SEQ ID NO:4. The first ATG (position 71) in the open reading frame was identified as the putative initiation codon since there is a purine at position -3 consistent with other eukaryotic translation initiation signals and an in-frame stop codon that occurs immediately upstream. The high A+T content (69%) of hemA and the codon usage predicted from the primary amino acid sequence of the hemA gene product are similar to that described for other reported cryptosporidial genes. Computer analysis of the nucleotide sequence using GRAIL (Guan et al., *Proc., The Eight IEEE Conference on AI Applications*, 1992, pp. 9–13) and the University of Wisconsin Genetics Computer Group sequence analysis package version 7.0, (Devereux et al., *Nucleic Acids Res.*, 1984, 12:387–395), predicted hemA to be a likely protein coding region. There were no identifiable polyadenylation signals in the remaining 180 bp of H4 insert downstream of the hemA stop codon. The 229-amino acid protein predicted by the hemA nucleotide sequence is predominantly hydrophilic and has a calculated molecular mass of about 26 kD. No membrane spanning regions or signal sequences are evident from the deduced primary amino acid sequence. Asparagine residues make up 11% of the predicted polypeptide. One potential N-glycosylation site is present, and there are numerous serine and threonine residues that could serve as sites of O-linked glycosylation. No conserved peptide motifs were found, but the tetrapeptide IENG is repeated four consecutive times within the carboxy terminus of the predicted protein. A BLAST search of the current DNA and protein databanks revealed no significant homologies to hemA or its predicted protein.

Karyotypic Southern blot analysis. To confirm that the 5.5 kb insert of H4 was cryptosporidial in origin, chromosomal DNA isolated from *C. parvum* oocysts was fractionated by pulsed field gel electrophoresis, capillary blotted to a nylon membrane and hybridized with a $^{32}$P-labeled 5.5 kb fragment. Five distinct chromosomal DNA bands were identified on ethidium bromide stained agarose gels. Hybridization studies mapped the cryptosporidial genomic region to the second smallest chromosome.

In vitro expression of the cryptosporidial protein. [$^{35}$S] methionine labeled plasmid-encoded proteins of H4 and the H4 deletion clones were expressed in maxicells of *E. coli* CSR603 to identify the cryptosporidial proteins encoded on the recombinant plasmids. A protein of about 22 kDa was apparent on autoradiographs of maxicell lysates from strains transformed with H4 and H4 deletion clones containing the complete hemA coding region, but not in lysates from transformants containing nonrecombinant pBluescript or a H4 deletion clone containing only a portion of hemA. The size of this protein is slightly smaller than the calculated molecular weight based on the predicted amino acid composition of the hemA encoded protein.

Hemolytic activity of H4. To further characterize the hemolytic activity of the H4 transformants, hemolytic assays were performed on culture supernatants and cell sonicates of H4 and pBluescript transformants. The H4 culture supernatants did not exhibit significant hemolytic activity when added to sheep erythrocytes, indicating that the hemolytic activity encoded on H4 was not actively secreted into the culture media. However, sonicates of H4 transformed cells displayed strong hemolytic activity when compared to sonicates of pBluescript transformed cells and to a 0.1% Triton-X 100 positive control (Table II). Incubation of erythrocytes with undiluted H4 cell sonicates resulted in almost complete erythrocyte lysis after four hours of incubation. Dilution of the H4 sonicates 1:10 with PBS prior to incubation resulted in about 50% lysis of the erythrocytes. Proteinase K digestion and heat treatment of the H4 sonicates prior to the assay markedly decreased their hemolytic activity, while the addition of $Ca^{++}$, $Mg^{++}$ and EDTA had no effect on the assay results. Storage of the undiluted cell sonicates at 4° C. and −20° C. for one week did not appreciably diminish the hemolytic activity. Undiluted sonicates assayed at different incubation temperatures, displayed similar hemolytic activity at room temperature that was only mildly decreased when incubated at 4° C. or on ice.

TABLE II

Location and Measurement of Hemolytic Activity In Overnight Cultures of H4 Transformants

| | % Hemolysis[a] | |
|---|---|---|
| | pBluescript | H4 |
| Culture supernatants | 4 | 7 |
| Cell sonicates[d] | | |
| Undiluted | 14[b] | 94[b] |
| Diluted[c] | 1 | 52 |

[a]Hemolytic activity is expressed as a percentage of sheep erythrocytes lysed after 4 hours at 37° C. Percent hemolysis is calculated based on Triton-X 100 control for 100% lysis. All assays were performed in duplicate.
[b]Protein concentration 2.7 mg/ml
[c]Diluted 1:10 in phosphate-buffered saline (PBS)
[d]Cell pellets were resuspended in 1 ml PBS and sonicated on ice in multiple 10 second bursts with a Branson ultrasonifier.

Transcriptional analysis of hemA. Since membrane disruption is an integral part of the cryptosporidial life cycle, it is reasonable to expect that membranolytic proteins are made in many, if not all, of the protozoan's life stages. In order to determine whether hemA is actively transcribed during the sporozoite life stage, RT-PCR analysis was performed on total RNA isolated from excysted sporozoites using primers designed to amplify a 369 bp fragment internal to hemA. Positive control reaction were performed using primers designed to amplify a 295 bp region within a *C. parvum* actin gene (Kim et al., *Mol. Biochem. Parasitol*, 1992, 50:105–114). Agarose gel electrophoresis of the RT-PCR reactions yielded the expected gene fragments for each primer set. All amplification products were verified by Southern blot hybridization studies using radiolabeled probes that had been previously confirmed by nucleotide sequence analysis to match the expected regions of hemA or the cryptosporidial actin gene. Amplification with the hemA primers gave an additional band of 270 bp that did not hybridize to the hemA probe. Negative control reactions which omitted either the reverse transcriptase or template did not yield a PCR product.

Adult SCID mice experimentally infected with cryptosporidial oocysts are known to contain numerous organisms in the villous and crypt mucosa of their anterior colons by 60 days post inoculation. In order to determine whether hemA is actively transcribed by *C. parvum* during infection of mammalian hosts, RT-PCR analysis of total RNA isolated from the ascending colons of infected mice was also performed. RNA isolated from the proximal colons of age-matched uninfected mice was used in control reactions. A 369 bp amplification product was present on agarose gels of reactions performed with RNA isolated from the intestines of infected mice but not with RNA isolated from uninfected mice. Mouse β-actin primers were included in the RT-PCR reactions as a positive control to verify that intact RNA had been isolated from the uninfected mice. Similar results were obtained when the cDNAs generated from the infected and control mice were tested with primers to the *C. parvum* actin gene. Negative control reactions and Southern blot verification of the amplified products were performed as described above.

DETECTION OF *C. parvum*

The present invention provides an improved method for diagnosis of cryptosporidiosis and further provides oligonucleotide probes and polymerase chain reaction primers specific to *C. parvum*.

The invention provides a method of detecting and identifying *C. parvum* specifically by identifying DNA of SEQ ID NO:1, 2, 3 or 4 or characteristic subsequences thereof by use of hybridization probing and/or nucleotide sequence amplification by the polymerase chain reaction (PCR). Amplification of these sequences by the PCR provides direct indication of positive result through observation of product formation of predicted size or confirmatory hybridization probing. The specific oligonucleotide probes and primers of the invention can be applied to suitably treated samples (e.g., surface water or feces) to detect *Cryptosporidium parvum*.

Probing can be carried out by using radiolabeled probes in Southern Blotting, but use of other probing techniques is also provided, e.g., by tagging oligonucleotides complementary to the target sequence with a marker, such as biotin or a fluorescent agent, and relating presence of bound marker with a positive result, or by using biotin tag as active agent in an ELISA in the known manner or detecting fluorescence.

The present invention particularly provides a method capable of the detection of *C. parvum* oocysts in contaminated water, a task requiring extremely sensitive techniques.

Typically the specific sequence amplification primers of the invention are applied to crude preparations of oocysts, fecal or water samples, together with chain reaction reagents and the performance of the reaction is assessed under these conditions. Oocysts may be isolated by concentration from water for releasing DNA according to isolation methods well known to those of ordinary skill in the art. Amplification using PCR or Ligase Chain Reaction (LCR) can then be used to detect the presence of Cryptosporidium.

A first aspect of the present invention provides a method for the detection and/or identification of *C. parvum* organisms, or polynucleic acid specific thereto, comprising determining the presence of the nucleic acid sequences SEQ ID NO:1, or the complementary sequence SEQ ID NO:2, or the nucleic acid sequence SEQ ID NO:3 or its complementary sequence, SEQ ID NO:4, or characteristic subsequences of SEQ ID NO:1–4, in polynucleic acid present in or derived from a sample under investigation, and relating the presence thereof to presence of *C. parvum* or polynucleic acid thereof.

In a preferred embodiment of this aspect of the present invention the method comprises hybridization probing polynucleic acid present in or derived from a sample under investigation with an oligonucleotide that is capable of specific hybridization with sequences characteristic of the sequences SEQ ID NO:1–4 and relating the occurrence of products of the hybridization with the presence of *C. parvum* or polynucleic acid thereof. Such hybridization may be carried out by any of the conventionally known methods, e.g. by Southern Blotting or one of the tagging methods referred to above.

The term "characteristic of" as used herein refers to sequences that have a sufficient number of consecutive bases which are homologous with the sequence of interest to be considered statistically highly likely to be derived from that sequence. Thus herein a "characteristic sequence" is one identical to any 10 consecutive bases or more of the sequences described herein, in this case SEQ ID NO:1–4. Preferred probes for identifying such sequences are SEQ ID N:5–8.

The specificity of the probing is controlled in the known manner by selecting stringency conditions such that the chosen probe will not hybridize with sequences found in other organisms that are known to be present in or considered likely to be found in such sample. This can be determined by carrying out control experiments. Furthermore, probes can be confirmed as specific by comparing their complementary sequences to sequences found in other known organisms. Such comparison can be readily made using computer databases, such as EMBL or GENBANK, whereby rapid comparison of sequences can be made.

The present invention further provides polynucleotide probes suitable for this method, preferably comprising a polynucleotide subunit of one of SEQ ID NO:1–4, said probe being optionally labeled in known manner, e.g. by incorporation of a radioactive $^{32}P$), chemical or biological label into its structure; most preferably consisting of these sequences.

In a preferred embodiment the present invention provides a method for the detection and/or identification of *C. parvum* organisms or nucleic acid specific thereto comprising use of specific sequence amplification, e.g., the polymerase chain reaction, to amplify prepared subunits of SEQ ID NO:1–4. The use of primers in the known manner may be made to target these sequences to provide an all or nothing amplification indicative of the presence of *C. parvum*.

Thus, for example, for the polymerase chain reaction, forward and reverse PCR primers having 5' end sequences SEQ ID NO:5 and SEQ ID NO:6, respectively, may be used, with or without 5' end non-hybridizing extensions:

| | |
|---|---|
| 5' ATG CTA CAC AAC ATG GAG AAG G 3' | SEQ ID NO:5 |
| 5' AGT TAT CCA ATC CCA ATT GGT 3' | SEQ ID NO:6 | for example, consisting of these sequences or any other primers which specifically provide for PCR amplification of all or a portion of SEQ ID NO:1 or SEQ ID NO:2. It will be understood by those skilled in the art that when it is desired to use the ligase chain reaction rather than PCR, longer primers will be required, having a smaller gap between them on the target sequence.

In another example, preferred PCR primers found to be specific for amplification of DNA characteristic of SEQ ID NO: 3 and 4 have 5' end SEQ ID NO:7 (forward primer) and SEQ ID NO:8 (reverse primer):

| | |
|---|---|
| 5' AAA ATG CCA TGT AAA TCA GCG 3' | SEQ ID NO:5 |
| 5' TCC GAA TCC AAG AAA ACC AC 3' | SEQ ID NO:5 |

Specific hybridization may be carried out in each case with hybridization conditions stringent enough to exclude interfering organisms and genomic DNA from other Cryptosporidium organisms while being of low enough stringency to allow hybridization with the parvum sequences. The determination of such conditions will be readily made by those skilled in the art by use of simple control experiments and the protocols outlined in the examples provided herein.

The present invention further provides a method for detecting or identifying C. parvum organisms or nucleic acid sequences specific thereto comprising:

(a) mixing a sample suspected of comprising said organisms and/or nucleic acid sequences with polymerase chain reaction or ligase chain reaction reagents, and respective primers targeted to specifically amplify a polynucleotide sequence within SEQ ID NO:1 and/or 2;

(b) subjecting the mixture to conditions under which amplification of at least one sequence characteristic of SEQ ID NO:1 and/or 2 present will occur; and (c) relating the production of a polymerase chain reaction product corresponding in size to the amplified subsequence to the presence of C. parvum organisms or nucleic acid sequences specific thereto.

Preferably, the polynucleotide sequence amplified is a double stranded sequence found within SEQ ID NO:1 and 2, which is amplified by PCR primers of SEQ ID NO:5 and 6 described in the sequence listing given herein, but may be any polynucleotide sequence characteristic of all or a portion of SEQ ID NO:1 or SEQ ID NO:2.

The present invention further provides a method for detecting or identifying C. parvum organisms or nucleic acid sequences specific thereto comprising:

(a) mixing a sample suspected of comprising said organisms and/or nucleic acid sequences with polymerase chain reaction or ligase chain reaction reagents, and respective primers targeted to specifically amplify a polynucleotide sequence within SEQ ID NO:3 and/or 4;

(b) subjecting the mixture to conditions under which amplification of at least one sequence characteristic of SEQ ID NO:3 and/or 4 present will occur; and (c) relating the production of a polymerase chain reaction product corresponding in size to the amplified subsequence to the presence of *C. parvum* organisms or nucleic acid sequences specific thereto.

Preferably, the polynucleotide sequence amplified is a double stranded sequence found within SEQ ID NO:3 and 4, which is amplified by PCR primers of SEQ ID NO:7 and 8 described in the sequence listing given herein, but may be any polynucleotide sequence characteristic of all or a portion of SEQ ID NO:3 or SEQ ID NO:4.

Again, in order to ensure specific amplification of the target sequence it is convenient to determine the degree of specificity required of the primers to be selected by either using control experiments using DNA of organisms likely to be found in the samples to be tested as controls with which the selected primers should not initiate a polymerase chain reaction. In a further method of selecting primers, the primer nucleotide sequence contemplated for use may be compared to known sequences on databases such a EMBL and Genbank where a finding of low homology with recorded sequences, particularly in the area of the primer 5' end sequence, indicates suitability for specific amplification.

Where verification of production of a PCR (or LCR) product or a native unamplified sequence as being one of *C. parvum* is intended then probing may be carried out using a labeled probe specific for the sequences above, e.g., probes comprising any of the sequences SEQ ID NO:5–8 or double stranded sequences containing these. Other probe sequences selected from the aforesaid sequences will also be derivable by the person skilled in the art by use of control experiments and/or databases referred to above, but it is generally recognized that sequences complementary to 10 or more consecutive bases of the target polynucleic acid will be specific enough in binding for verification of presence of such sequences.

Preferably, where PCR is used, the primers should be of 6 or more bases long, more preferably 10 to 30 bases long and most preferably from 15 to 21 bases long.

The unamplified or amplified polynucleotide sequence may be identified by hybridization probing using a suitably labeled oligonucleotide that is capable of specific hybridization with the sequence SEQ ID NO:1–4 or double stranded sequences made up of these, or subunits thereof.

It will be understood by those skilled in the art that when any of the methods outlined above are being applied to whole organisms, rather than to nucleic acids derived from them, it will be necessary to incorporate a procedure for liberating nucleic acids from said organism before initiating amplification chain reaction conditions. The preferred forms of the present invention provide particular procedures whereby the sample to be tested is first suspended in a medium, e.g., a buffer, and then either sonicated or subjected to freeze/thaw cycles in buffer containing a reducing agent, e.g., dithiothreitol (DTT), in order to rupture the organisms, particularly their oocyst forms, and liberate the polynucleic acids. Particularly preferred are formats that isolate oocysts using antibodies to oocysts that have been tagged with metallic particles such that use of magnetic fields can recover individual oocyst/antibody complexes.

Using these preferred methods of the present invention it is possible to achieve detection or identification of Cryptosporidium organisms in oocyst form or otherwise. Preferably the sonication or freeze/thaw procedure is carried out in a medium which will form all or part of the PCR, LCR or probing medium, e.g. the 1×TE medium referred to below, together with a reducing agent, e.g. 1–2% DTT in buffer. Sonication is conveniently carried out using about 11 μm peak to peak. Alternatively, for freeze/thaw procedure, the sample containers can be conveniently immersed in a cryogenic liquid such as liquid nitrogen. Other methods for disrupting cell or oocyte structures to liberate nucleic acids into the PCR or LCR probing medium will be known to the skilled person and may be expected to be applicable before initiating the PCR, LCR and/or probing procedures.

In a still further aspect of the present invention there are provided test kits comprising one or more probes and/or primers of the present invention as described herein above, in addition to these probes and primers per se.

The method, primers and probes of the present invention will now be described by way of illustration only by reference to the following protocols and examples. Further variants of the method, primers and probes falling within the scope of the invention will occur to the person skilled in the art in the light of these.

EXAMPLE 1

POLYMERASE CHAIN REACTION DETECTION OF *C. PARVUM* NUCLEOTIDE SEQUENCES

Primer pair SEQ ID NO:5 and 6 or primer pair SEQ ID NO:7 and 8 may be used in the following reaction mix/conditions to amplify a DNA fragment from *C. parvum*.

Reaction mix (volume 50 μl)

dntp,s –250 μmoles primers –100 pmoles of each primer (SEQ ID NO:5 and 6 or SEQ ID NO: 7 and 8)

glycerol −5% v/v
Taq polymerase −2.5 units
1XTE (10 mm Tris.cl pH 8; 1 mm EDTA pH8)
Buffer
  5.5 mm MgCl$_2$
  50 mm KCl
  10 mm Tris.cl pH 8.3
plus the target nucleic acid to be amplified in a volume of 1–10 μl.

Reaction Conditions
  Initial denaturing step 94° C. for 3 minutes
  Denature 94° C. for 90 seconds)
  Anneal 50° C. for 120 seconds) 40 cycles
  Extend 72° C. for 120 seconds)
  Final extension 72° C. for 5 minutes The sample is then run on a 2% horizontal agarose gel, stained with ethidium bromide and viewed under UV illumination and compared to the sample gel with those from positive and negative DNA controls.

EXAMPLE 2

PCR HYBRIDIZATION PROBING

The DNA on the stained gel produced in Example 1 may be transferred onto a nylon filter (trademark-Hybond N) by Southern Blotting, denatured and hybridized with a $^{32}$P radiolabeled (multiprime labeling procedure) cloned C. parvum internal probe having SEQ ID NO:5 or another sequence characteristic of SEQ ID NO:1. After washing off non-specifically bound probe, the filter is exposed to X-ray film (autoradiography) for 12 hours or 7 days. Detection limits are respectively: 12 hours 0.3 fg, 7 days 0.03 fg of C. parvum DNA. It will be realized that the hybridization probe might be used directly on the sample DNA without PCR but that his will necessarily reduce sensitivity.

EXAMPLE 3

PREPARATION OF WHOLE OOCYSTS FOR PCR

A rapid protocol may be used for preparation of oocysts (the infective stage of Cryptosporidium) for PCR to avoid the long procedure associated with preparation of DNA.

1. The sample to be tested is resuspended in a solution of 1×X TE (see above); 1% dithiothreotol (approx. final volume is 100 μl) 2. The oocysts are broken open by a) 3 cycles of sonication for 10 seconds (11 μm peak to peak) with a 50 second rest, or b) 3 freeze/thaw cycles in liquid nitrogen. 3. The sample is then heated to 90° C. for 20 minutes. 4. Debris is pelleted by centrifugation at 13000 g for 5 minutes. 5. 1–10 μl of the supernatant is used as the template for PCR.

EXAMPLE 4

APPLICATION OF THE METHOD TO HUMAN AND ANIMAL FECAL SAMPLES

A human fecal sample is diluted 1/100 in 1×TE/2% DTT buffer, freeze thawed in liquid nitrogen five times, heated to 90° C. for 20 minutes, debris pelleted at 13,000 g for 5 minutes and the supernatant used as a template for PCR, as described above, for example, using primers described above.

UTILITY AS VACCINES

Applicants anticipate that proteins coded for by the DNA sequence described herein, in particular SEQ ID NO:1 and 3 or subunits thereof, such as the first and second open reading frames of SEQ ID NO:1 identified above, can be used to generate antibodies or cell mediated immunity which can inhibit the pathogenesis of C. parvum. A protein such as that shown in SEQ ID NO:9 could be used in a vaccine formulation to induce production of antibodies in vivo for warding off infection by C. parvum or for the production of antibodies for use in a serum formulation against an active C. parvum infection.

Methods for producing such vaccines and for producing sera are well known to those of ordinary skill in the art, such as exemplified by the methods used by B. Knapp et al. (Knapp et al., "Protection of Aotus Monkeys from Malaria Infection by Immunization with Recombinant Hybrid Proteins", Infection and Immunity, June 1992, pp. 2397–2401; the disclosure of which is hereby incorporated herein by reference). Vaccination schedules and dosages are also well known to those of ordinary skill in the art. Exemplary of such a schedule is to be vaccinated in dosages ranging from 20 to 50 to 100 to 160 μg with booster injections provided after 28 and 56 days.

Vaccination by Plasmid Injection

It is also contemplated that vaccination may be accomplished via direct intramuscular or intradermal injection of recombinant plasmid DNA. Humoral as well as cell-mediated immune response have been elicited against viral and parasite proteins in a variety of animals using plasmid injection as is well known to those of ordinary skill in the art. Direct DNA injection may also be used to induce partial to complete immunity against pathogen challenge. A vaccination methodology using plasmid injection is shown below.

Plasmid DNA Construction

A cDNA such as SEQ ID NO:1 or SEQ ID NO:3 or subunits thereof of C. parvum is subcloned into the pRC/CMV expression vector (Invitrogen, San Diego, Calif.) downstream of the human cytomegalovirus immediate early gene 1 promoter/enhancer region. To facilitate cloning and expression, the 5' end of the cDNA inset is extended with a BstX I site, a mammalian ribosome binding site sequence, and an ATG translational start site. The 3' end is extended to include a Not I site. Extension is performed by PCR using synthetic oligomer primers containing the respective extension sequences and either the first 35 bases of the 5' end of the cDNA or 35 bases in the distal 3' region of the cDNA. The resulting PCR product is directionally cloned as a BstXI-NotI fragment into pRC/CMV resulting in the production of the plasmid. Duplication of the cDNA sequence and the open reading frame is confirmed by sequencing the entire insert. Plasmid DNA is prepared by culture in E. coli strain DH5 in super broth media containing ampicillin. Following alkaline lysis, plasmid was purified by polyethylene glycol precipitation technique followed by phenol, phenol/chloroform, and two chloroform extractions.

DNA Injection and Vaccination

Plasmid DNA may be administered in a volume of 500 ul 0.15M NaCl using a needle and syringe, or a jet-injection apparatus. DNA may be administered through the skin using a vaccination schedule similar to the above.

Changes may be made in the construction and the operation of the various components, elements and assemblies described herein or in the steps or the sequence of steps of the methods described herein without departing from the spirit and scope of the invention as defined in the following claims.

What is claimed is:

1. A method for the detection of *Cryptosporidium parvum* organisms, or nucleic acid sequences specific thereto, comprising determining the presence of a nucleic acid sequence selected from the group consisting of SEQ ID NO:1, SEQ ID NO:2, SEQ ID NO:3, and SEQ ID NO:4, in nucleic acid present in, or derived from, a sample under investigation, wherein detection of said at least one nucleic acid sequence indicates the presence of *Cryptosporidium parvum* or nucleic acid sequences specific thereto in said sample.

2. The method of claim 1 wherein the method further comprises using a specific sequence amplification technique which requires at least one oligonucleotide primer that is capable of specifically hybridizing with a nucleotide sequence selected from the group consisting of SEQ ID NO:1 and SEQ ID NO:2 thereby forming at least one amplification product and wherein detection of said at least one amplification product indicates the presence of *Cryptosporidium parvum* or nucleic acid sequences specific thereto in said sample.

3. The method of claim 2 wherein the at least one oligonucleotide primer comprises from 10 to 30 consecutive bases of nucleic acid sequences SEQ ID NO:1 or SEQ ID NO:2.

4. The method of claim 2 wherein the at least one oligonucleotide primer comprises from 12 to 25 consecutive bases of nucleic acid sequences SEQ ID NO:1 or SEQ ID NO:2.

5. The method of claim 2 wherein the oligonucleotide primer comprises from 15 to 22 consecutive bases of nucleic acid sequences SEQ ID NO:1 or SEQ ID NO:2.

6. The method of claim 2 wherein the specific sequence amplification technique is carried out using the polymerase chain reaction and wherein the reaction uses a forward primer and a reverse primer.

7. The method of claim 6 wherein the forward and reverse primers comprise SEQ ID NO:5 and SEQ ID NO:6, respectively.

8. The method of claim 1 wherein the method further comprises using a specific sequence amplification technique which requires at least one oligonucleotide primer that is capable of specifically hybridizing with a nucleotide sequence selected from the group consisting of SEQ ID NO:3 and SEQ ID NO:4 thereby forming at least one amplification product and wherein detection of said at least one amplification product indicates the presence of *Cryptosporidium parvum* or nucleic acid sequences specific thereto in said sample.

9. The method of claim 8 wherein the at least one oligonucleotide primer comprises from 10 to 30 consecutive bases of nucleic acid sequences SEQ ID NO:3 or SEQ ID NO:4.

10. The method of claim 8 wherein the at least one oligonucleotide primer comprises from 12 to 25 consecutive bases of nucleic acid sequences SEQ ID NO:3 or SEQ ID NO:4.

11. The method of claim 8 wherein the at least one oligonucleotide primer comprises from 15 to 21 consecutive bases of nucleic acid sequences SEQ ID NO:3 or SEQ ID NO:4.

12. The method of claim 8 wherein the specific sequence amplification technique is carried out using the polymerase chain reaction and wherein the reaction uses a forward primer and a reverse primer.

13. The method of claim 12 wherein the forward and reverse primers comprise SEQ ID NO:7 and SEQ ID NO:8, respectively.

14. A method for the detection of *Cryptosporidium parvum* organisms or nucleic acid sequences specific thereto comprising:

reacting a sample suspected of comprising said organisms and/or nucleic acid sequences the in a specific sequence amplification reaction using specific sequence amplification reaction reagents and primers for said amplification, said primers capable of specifically amplifying a polynucleotide sequence selected from the group consisting of SEQ ID NO:1, SEQ ID NO:2, SEQ ID NO:3, and SEQ ID NO:4 thereby forming at least one amplification product when said organisms and/or nucleic acid sequences thereof are present in said sample; and wherein detection of said at least one amplification product indicates the presence of *Cryptosporidium parvum* or nucleic acid sequences specific thereto in said sample.

15. The method of claim 14 wherein the specific sequence amplification reaction is the polymerase chain reaction and the primers comprise SEQ ID NO:5 and SEQ ID NO:6.

16. The method of claim 14 wherein the specific sequence amplification reaction is the polymerase chain reaction and the primers comprise SEQ ID NO:7 and SEQ ID NO:8.

17. The method of claim 14 further comprising liberating nucleic acids from said organisms before initiating amplification conditions.

18. The method of claim 17 wherein the liberating step further comprises either sonicating or subjecting the organisms to freeze/thaw cycles in order to rupture the organisms and liberate the nucleic acids therefrom.

19. The method of claim 14 wherein the primers used in the reacting step have been labeled with a radioactive, chemical or biological label.

20. A diagnostic kit comprising at least one primer suitable for the amplification of a sequence selected from the group consisting of SEQ ID NO:1, SEQ ID NO:2, SEQ ID NO:3 and SEQ ID NO:4 for detecting *Cryptosporidium parvum* in a sample wherein the primer is a subsequence of at least one of said group.

21. The diagnostic kit of claim 20 wherein the primer is further defined as being labeled by incorporation of a radioactive, chemical or biological label into its structure.

22. An isolated DNA fragment comprising SEQ ID NO:1 or an open reading frame of SEQ ID NO:1.

23. The DNA fragment of claim 22 inserted into a vector.

24. An isolated purified polypeptide coded for by SEQ ID NO:1 or an open reading frame of SEQ ID NO:1.

25. An oligonucleotide primer comprising from 10 to 30 consecutive bases of nucleic acid sequences SEQ ID NO:1 or SEQ ID NO:2.

26. An isolated DNA fragment comprising SEQ ID NO:3 or an open reading frame of SEQ ID NO:3.

27. The DNA fragment of claim 26 inserted into a vector.

28. An isolated purified polypeptide coded for by SEQ ID NO:3 or an open reading frame of SEQ ID NO:3.

29. An oligonucleotide primer comprising from 10 to 30 consecutive bases of nucleic acid sequences SEQ ID NO:3 or SEQ ID NO:4.

30. An isolated DNA fragment comprising SEQ ID NO:2.

31. The DNA fragment of claim 30 inserted into a vector.

32. An isolated DNA fragment comprising SEQ ID NO:4.

33. The DNA fragment of claim 32 inserted into a vector.

* * * * *

UNITED STATES PATENT AND TRADEMARK OFFICE
CERTIFICATE OF CORRECTION

PATENT NO. : 5,693,472
DATED : December 2, 1997
INVENTORS : Marilyn I. Steele et al.

It is certified that error appears in the above-identified patent and that said Letters Patent is hereby corrected as shown below:

```
Column 12, line 59, "SEQ ID NO:5" should be
-- SEQ ID NO:7 --.
Column 12, line 60, "SEQ ID NO:5" should be
-- SEQ ID NO:8 --.
Column 13, line 57, "a" should be -- as --.
Column 15, line 35, "his" should be -- this --.
Column 30, line 6, "the" should be -- thereof --.
```

Signed and Sealed this

Twenty-second Day of September, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1298 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v i ) ORIGINAL SOURCE:
        ( A ) ORGANISM: Cryptosporidium parvum
        ( G ) CELL TYPE: Unicellular Organism ( v i i ) IMMEDIATE SOURCE:
        ( A ) LIBRARY: genomic
        ( B ) CLONE: INV38G ( x ) PUBLICATION INFORMATION: unpublished
        ( K ) RELEVANT RESIDUES IN SEQ ID NO: from 1 to 1298

( x i ) SEQUENCE DESCRIPTION: SEQ ID NO:1:

```
atcctctttc cacaaagtat ataaataagt acctggtatc agaccataat gaaacacttt   60
ctttgcatat ctgtaccaaa ataggataaa tttatggtat atctgcgtaa tttaatagaa  120
aataaatttt tcatgagtaa taaggagtta gtagtttatt cttaccttta gaaatgccac  180
ttttaattat gttcaaatat atttgattca atttgagaat cttatcatat aaaagtttgg  240
agtatacttg tgagtatctc attatttcaa tatttcaaag tataatagaa atgcaatatt  300
aattattatt cagaagtttt ctctgtttta ttttatttta ttttcaaag tattaggaat   360
ttaggaaata attataactc cattcggcgc caacgggccc ccacagtcat aattgacagc  420
caatgtgtga aaaatatta attaaaagtg gaatcagaga ataaatttgc atcaatctaa  480
aaagatattt ttctaaaatg tccaatattt cagcaattaa tttcttttca gaaagtaagt  540
ttttgtgat tctttgtga aatatatat tctttgagtg gatttacaag taataactaa    600
cttttctatg attctataga cattgggatt actggatttg actcagaaaa tgctccttt   660
atggctttca aggtaagtta aataagattt aatttgcaat gtagctttta gtttaatttg  720
gattgatttt ttttatttag gaacttttg ataactctat agatgcatgt aataataagg   780
caaaagcaga gtggcatgat tttccaaaaa aaatagaaat ctctgtgaat tttgagaatt  840
tagaattgga tgatcaggta agtaaaatac aggactagta ttaataaatt tgatttttta  900
ttaaaattgg tttgaacttt aaggcaagaa taaacatcat tgtaagagat acaggatgcg  960
gaatacctt agaatccatt gacctattgg gaactctttt tggaacaaag tgagtttaaa  1020
tattaattgt atttaaagtg attgattaaa ttttaattc tgattcatct tttagtaaga  1080
aaataaataa aagagattct tattatacag gacaatttgg ggtaggcctt aaaatgatat  1140
tactttatgc tacacaacat ggagaaggaa acgttaaagt taagatgaga atgggaaaca  1200
agatttggga gtttactctg ctttgtaacc tgaatgatgg atcttttat gtagggaata   1260
gtgagagttt tgattatacc aattgggatt ggataact                           1298
```

( 2 ) INFORMATION FOR SEQ ID NO:2:

( i ) SEQUENCE CHARACTERISTICS:
        ( A ) LENGTH: 1298 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: yes ( v i ) ORIGINAL SOURCE:
        ( A ) ORGANISM: Cryptosporidium parvum
        ( G ) CELL TYPE: Unicellular organism ( v i i ) IMMEDIATE SOURCE:
        ( A ) LIBRARY: genomic
        ( B ) CLONE: INV38G ( x ) PUBLICATION INFORMATION: unpublished
        ( K ) RELEVANT RESIDUES IN SEQ ID NO: from 1 to 1298

( x i ) SEQUENCE DESCRIPTION: SEQ ID NO:2:

```
taggagaaag gtgtttcata tatttattca tggaccatag tctggtatta ctttgtgaaa    60
gaaacgtata gacatggttt tatcctattt aaataccata tagacgcatt aaattatctt   120
ttatttaaaa agtactcatt attcctcaat catcaaataa agaatggaat ctttacggtg   180
aaaattaata caagtttata taaactaagt taaactctta gaatagtata ttttcaaacc   240
tcatatgaac actcatagag taataaagtt ataaagtttc atattatctt tacgttataa   300
ttaataataa gtcttcaaaa gagacaaaat aaaataaaat aaaagtttc ataatcctta    360
aatcctttat taatattgag gtaagccgcg gttgcccggg ggtgtcagta ttaactgtcg   420
gttacacact tttttataat taatttcac cttagtctct ttattaaacg tagttagatt    480
tttctataaa aagattttac aggttataaa gtcgttaatt aagaaaagt ctttcattca    540
aaaacacta agaaacact ttatatataa agaaactcac ctaaatgttc attattgatt     600
gaaagatac taagatatct gtaaccctaa tgacctaaac tgagtcttt acgaggaaaa     660
taccgaaagt tccattcaat ttattctaaa ttaaacgtta catcgaaaat caaattaaac   720
ctaactaaaa aaataaatc cttgaaaaac tattgagata tctacgtaca ttattattcc    780
gttttcgtct caccgtacta aaaggttttt tttatcttta gagacactta aaactcttaa   840
atcttaacct actagtccat tcatttatg tcctgatcat aattatttaa actaaaaaat    900
aattttaacc aaacttgaaa ttccgttctt atttgtagta acattctcta tgtcctacgc   960
cttatggaaa tcttaggtaa ctggataacc cttgagaaaa accttgtttc actcaaattt  1020
ataattaaca taaatttcac taactaattt aaaaattaag actaagtaga aaatcattct  1080
tttatttatt ttctctaaga ataatatgtc ctgttaaacc ccatccggaa ttttactata  1140
atgaaatacg atgtgttgta cctcttcctt tgcaatttca attctactct taccctttgt  1200
tctaaaccct caaatgagac gaaacattgg acttactacc tagaaaata catcccttat   1260
cactctcaaa actaatatgg ttaaccctaa cctattga                          1298
```

( 2 ) INFORMATION FOR SEQ ID NO:3:

( i ) SEQUENCE CHARACTERISTICS:
        ( A ) LENGTH: 943 Base Pairs
        ( B ) TYPE: Nucleic Acid
        ( C ) STRANDEDNESS: Single
        ( D ) TOPOLOGY: Linear (  i  i  ) MOLECULE TYPE: genomic DNA (  i  i  i  ) HYPOTHETICAL: no (  i  v  ) ANTI-SENSE: no (  v  i  ) ORIGINAL SOURCE:
    (  A  ) ORGANISM: Cryptosporidium parvum
    (  G  ) CELL TYPE: unicellular organism (  v  i  i  ) IMMEDIATE SOURCE:
    (  A  ) LIBRARY: genomic
    (  B  ) CLONE: HemA (  x  ) PUBLICATION INFORMATION: unpublished
    (  K  ) RELEVANT RESIDUES IN SEQ ID NO: from 1 to 943

(  x  i  ) SEQUENCE DESCRIPTION: SEQ ID NO:3:

```
aatatactat aaattaatcc tatattttta atttataatt gaaactaatt aaataaaata      60
ataaggtgaa atg agc caa aaa ata gat ttg aat caa ggt gaa aga act gag    112
            Met Ser Gln Lys Ile Asp Leu Asn Gln Gly Glu Arg Thr Glu
             1           5                  10 tca aaa tgt cca gaa acg ctt aat gaa ttt tct aat atg tat aag cat aaa  163
Ser Lys Cys Pro Glu Thr Leu Asn Glu Phe Ser Asn Met Tyr Lys His Lys
 15              20                  25                  30 aaa atg cca tgt aaa tca gcg ctg aac ttt ggt gaa aat att ata aat atg  214
Lys Met Pro Cys Lys Ser Ala Leu Asn Phe Gly Glu Asn Ile Ile Asn Met
             35                  40                  45 gga gct cca agt ttt ata cca gaa tat cca aca gct tat tat tct aac cca  265
Gly Ala Pro Ser Phe Ile Pro Glu Tyr Pro Thr Ala Tyr Tyr Ser Asn Pro
 50                  55                  60                      65 gaa gtt atg aat caa gga ata aat tca tta gtg gat aca aaa caa cta tat  316
Glu Val Met Asn Gln Gly Ile Asn Ser Leu Val Asp Thr Lys Gln Leu Tyr
                 70                  75                  80 gac tat tca tcc cct gta ggt gat ctt gaa aaa acc att gaa cat tac aaa  367
Asp Tyr Ser Ser Pro Val Gly Asp Leu Glu Lys Thr Ile Glu His Tyr Lys
         85                  90                  95 atg agt cat gaa ata gga tgg aat gca agt aat tct ttc act cct aca aat  418
Met Ser His Glu Ile Gly Trp Asn Ala Ser Asn Ser Phe Thr Pro Thr Asn
100             105                 110                 115 tct ggt tct ttg gaa ctt ttc caa ttt gaa aga aga gat agt cct gtc gct  469
Ser Gly Ser Leu Glu Leu Phe Gln Phe Glu Arg Arg Asp Ser Pro Val Ala
                120                 125                 130 gtt gat act tta aaa aat tac cca tct ttt gag aga atg aat agt ggt ttt  520
Val Asp Thr Leu Lys Asn Tyr Pro Ser Phe Glu Arg Met Asn Ser Gly Phe
135                 140                 145                     150 ctt gga ttc gga aga aaa cct tct aat tca ata ttt tct att gga caa aaa  571
Leu Gly Phe Gly Arg Lys Pro Ser Asn Ser Ile Phe Ser Ile Gly Gln Lys
                155                 160                 165 ctt gaa aga ctc tct tct aat gaa ata atc aac aat atc aat acc ctt cct  622
Leu Glu Arg Leu Ser Ser Asn Glu Ile Ile Asn Asn Ile Asn Thr Leu Pro
        170                 175                 180 gaa att gaa aat ggt att gag aac ggt att gaa aat gga att gaa aat gga  673
Glu Ile Glu Asn Gly Ile Glu Asn Gly Ile Glu Asn Gly Ile Glu Asn Gly
185                 190                 195                 200 gat att cct cac gtt gat ttg gag caa tat aca caa tta tct tac ttt gaa  724
Asp Ile Pro His Val Asp Leu Glu Gln Tyr Thr Gln Leu Ser Tyr Phe Glu
            205                 210                 215 aaa tat atc aat ttt aac att gac caa att aag tgaatccatt tcttaaatat    777
Lys Tyr Ile Asn Phe Asn Ile Asp Gln Ile Lys
    220                 225 aactactttt tataaccaaa aatgctatga aacaaatcat ttttgcaaaa tatattggaa    837
tattattaga tttatgaaat atcaagctgt tcaaaagaat agcctgatac tccacgtaaa    897
```
atttgtaata ttgaaaagga atagtaactc ccaggaataa tacaaa 943

(2) INFORMATION FOR SEQ ID NO:4:

(i) SEQUENCE CHARACTERISTICS:
        (A) LENGTH: 943 base pairs
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: yes (vi) ORIGINAL SOURCE:
        (A) ORGANISM: Cryptosporidium parvum
        (G) CELL TYPE: Unicellular organism (vii) IMMEDIATE SOURCE:
        (A) LIBRARY: genomic
        (B) CLONE: HemA (x) PUBLICATION INFORMATION: unpublished
        (K) RELEVANT RESIDUES IN SEQ ID NO: from 1 to 943

(xi) SEQUENCE DESCRIPTION: SEQ ID NO:4:

```
ttatatgata tttaattagg atataaaaat taaatattaa cttgattaa tttatttat  60
tattccactt tactcggttt tttatctaaa cttagttcca cttcttgac tcagttttac 120
aggtctttgc gaattactta aaagattata catattcgta ttttttacg gtacatttag 180
tcgcgacttg aaaccacttt tataatattt atacccttga ggttcaaaat atggtcttat 240
aggttgtcga ataataagat tgggtcttca atacttagtt cctatttaa gtaatcacct 300
atgttttgtt gatatactga taagtagggg acatccacta gaactttttt ggtaacttgt 360
aatgttttac tcagtacttt atcctacctt acgttcatta agaaagtgag gatgtttaag 420
accaagaaac cttgaaaagg ttaaactttc ttctctatca ggacagcgac aactatgaaa 480
ttttttaatg ggtagaaaac tctcttactt atcaccaaaa gaacctaagc cttcttttgg 540
aagattaagt tataaaagat aacctgtttt tgaactttct gagagaagat tactttatta 600
gttgttatag ttatgggaag gactttaact tttaccataa ctcttgccat aactttacc  660
ttaacttta cctctataag gagtgcaact aaacctcgtt atatgtgtta atagaatgaa 720
acttttata tagttaaaat tgtaactggt ttaattcact taggtaaaga atttatattg 780
atgaaaaata ttggttttta cgatactttg tttagtaaaa acgttttata taaccttata 840
ataatctaaa tactttatag ttcgacaagt tttcttatcg gactatgagg tgcattttaa 900
acattataac ttttccttat cattgagggt ccttattatg ttt                 943
```

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: yes (vi) ORIGINAL SOURCE:
        (A) ORGANISM: Cryptosporidium parvum (G) CELL TYPE: Unicellular organism (vii) IMMEDIATE SOURCE:
                (A) LIBRARY: genomic
                (B) CLONE: INV38G (x) PUBLICATION INFORMATION: unpublished (xi) SEQUENCE DESCRIPTION: SEQ ID NO:5:

ATG CTA CAC AAC ATG GAG AAG G                                                           22

(2) INFORMATION FOR SEQ ID NO:6:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: genomic DNA (iii) HYPOTHETICAL: no (iv) ANTI-SENSE: yes (vi) ORIGINAL SOURCE:
                (A) ORGANISM: Cryptosporidium parvum
                (G) CELL TYPE: Unicellular organism (vii) IMMEDIATE SOURCE:
                (A) LIBRARY: genomic
                (B) CLONE: INV38G (x) PUBLICATION INFORMATION: unpublished (xi) SEQUENCE DESCRIPTION: SEQ ID NO:6:

AGT TAT CCA ATC CCA ATT GGT                                                             21

(2) INFORMATION FOR SEQ ID NO:7:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: genomic DNA (iii) HYPOTHETICAL: no (iv) ANTI-SENSE: no (vi) ORIGINAL SOURCE:
                (A) ORGANISM: Cryptosporidium parvum
                (G) CELL TYPE: Unicellular organism (vii) IMMEDIATE SOURCE:
                (A) LIBRARY: genomic
                (B) CLONE: HemA (x) PUBLICATION INFORMATION: unpublished (xi) SEQUENCE DESCRIPTION: SEQ ID NO:7:

AAA ATG CCA TGT AAA TCA GCG                                                             21

(2) INFORMATION FOR SEQ ID NO:8:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: genomic DNA ( i i i ) HYPOTHETICAL: no ( i v ) ANTI-SENSE: yes ( v i ) ORIGINAL SOURCE:
    ( A ) ORGANISM: Cryptosporidium parvum
    ( G ) CELL TYPE: Unicellular ( v i i ) IMMEDIATE SOURCE:
    ( A ) LIBRARY: genomic
    ( B ) CLONE: HemA ( x ) PUBLICATION INFORMATION: unpublished ( x i ) SEQUENCE DESCRIPTION: SEQ ID NO:8:

TCC GAA TCC AAG AAA ACC AC                                                                                     20

( 2 ) INFORMATION FOR SEQ ID NO:9:

( i ) SEQUENCE CHARACTERISTICS:
    ( A ) LENGTH: 229 Amino acids
    ( B ) TYPE: Amino acid
    ( D ) TOPOLOGY: Linear ( i i ) MOLECULE TYPE: protein ( x ) PUBLICATION INFORMATION: unpublished
    ( K ) RELEVANT RESIDUES IN SEQ ID NO: from 1 to 229

( x i ) SEQUENCE DESCRIPTION: SEQ ID NO:9:

```
Met Ser Gln Lys Ile Asp Leu Asn Gln Gly Glu Arg Thr Glu Ser Lys
 1               5                  10                  15

Cys Pro Glu Thr Leu Asn Glu Phe Ser Asn Met Tyr Lys His Lys Lys
                20                  25                  30

Met Pro Cys Lys Ser Ala Leu Asn Phe Gly Glu Asn Ile Ile Asn Met
            35                  40                  45

Gly Ala Pro Ser Phe Ile Pro Glu Tyr Pro Thr Ala Tyr Tyr Ser Asn
        50                  55                  60

Pro Glu Val Met Asn Gln Gly Ile Asn Ser Leu Val Asp Thr Lys Gln
65                  70                  75                  80

Leu Tyr Asp Tyr Ser Ser Pro Val Gly Asp Leu Glu Lys Thr Ile Glu
                85                  90                  95

His Tyr Lys Met Ser His Glu Ile Gly Trp Asn Ala Ser Asn Ser Phe
            100                 105                 110

Thr Pro Thr Asn Ser Gly Ser Leu Glu Leu Phe Gln Phe Glu Arg Arg
        115                 120                 125

Asp Ser Pro Val Ala Val Asp Thr Leu Lys Asn Tyr Pro Ser Phe Glu
    130                 135                 140

Arg Met Asn Ser Gly Phe Leu Gly Phe Gly Arg Lys Pro Ser Asn Ser
145                 150                 155                 160

Ile Phe Ser Ile Gly Gln Lys Leu Glu Arg Leu Ser Ser Asn Glu Ile
                165                 170                 175

Ile Asn Asn Ile Asn Thr Leu Pro Glu Ile Glu Asn Gly Ile Glu Asn
            180                 185                 190

Gly Ile Glu Asn Gly Ile Glu Asn Gly Glu Ile Pro His Val Asp Leu
        195                 200                 205

Glu Gln Tyr Thr Gln Leu Ser Tyr Phe Glu Lys Tyr Ile Asn Phe Asn
    210                 215                 220

Ile Asp Gln Ile Lys
225
```